United States Patent [19]

Kramer et al.

[11] 4,294,765
[45] Oct. 13, 1981

[54] CIS-LACTONE PYRETHROID INTERMEDIATES

[75] Inventors: Petrus A. Kramer; Pieter A. Verbrugge, both of Amsterdam, Netherlands

[73] Assignee: Shell Oil Company, Houston, Tex.

[21] Appl. No.: 200,227

[22] Filed: Oct. 23, 1980

[30] Foreign Application Priority Data

Nov. 1, 1979 [GB] United Kingdom ............... 37858/79

[51] Int. Cl.³ .......................................... C07D 307/93
[52] U.S. Cl. .......................................... 260/343.3 R
[58] Field of Search .................................. 260/343.3 R

[56] References Cited

U.S. PATENT DOCUMENTS 4,166,063  8/1979  Martel et al. ................. 260/343.3 R
4,219,562  8/1980  Roman ........................ 260/343.3 R

OTHER PUBLICATIONS

Methoden der Organischen Chemie (Houben–Wehyl), V1/2, p. 611 (1963).
Staninets, V. I. et al., Russian Chemical Reviews, 40(3), pp. 272–283 (1971).

Primary Examiner—John M. Ford
Assistant Examiner—Jane T. Fan

[57] ABSTRACT

Isolation of cis acids of the formula

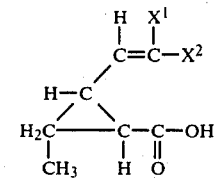

wherein each of the groups $X^1$ and $X^2$ represents a fluorine, chlorine or bromine atom or a hydrocarbyl group, from a mixture of cis and trans acids of this formula, by idolactonization, forming novel cis-lactones of the formula

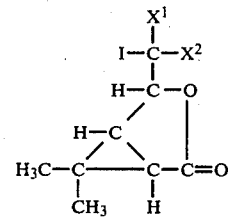

isolation of these cis-lactones and reduction thereof to the said cis acids.

The process may be used for the isolation of cis precursors to insecticides from mixtures with their trans isomers.

3 Claims, No Drawings

CIS-LACTONE PYRETHROID INTERMEDIATES

BACKGROUND OF THE INVENTION

1. Field of the Invention

The present invention relates to new cis-lactones, to processes for their preparation and to their use for the separation of cis/trans isomers of pyrethroid carboxylic acids.

2. Description of the Prior Art

Synthetic pyrethroids combine exceptionally good insecticidal properties with a very low mammalian toxicity. They are of considerable interest to the agrochemical industry and much effort has been expended in finding economic routes to them and to their principal intermediates.

The general formula of one class of these pyrethroids may be represented as follows:

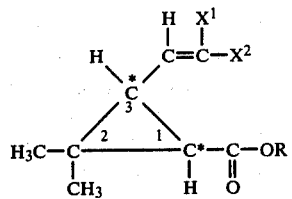
(I)

wherein each asterisk denotes an asymmetric carbon atom, each of the groups $X^1$ and $X^2$ represents a fluorine, chlorine or bromine atom or a hydrocarbyl group and R is a radical known to impart insecticidal activity to the molecule, for example 3-phenoxybenzyl or alpha-cyano-3-phenoxybenzyl. It is known that the stereo-isomeric form of the acid part of the ester of formula I should be 1R,cis for maximum insecticidal activity, i.e. the absolute configuration at carbon atom 1 is R and the two hydrogen atoms on carbon atoms 1 and 3 are in a cis relationship. This nomenclature is known as the Elliott nomenclature and is defined in M. Elliott et al., Nature, 1974, 248, 710.

It follows, therefore, that if these cis esters of formula I are to be prepared, it would be useful if one could dispose of a process for the isolation of cis carboxylic acids of the general formula:

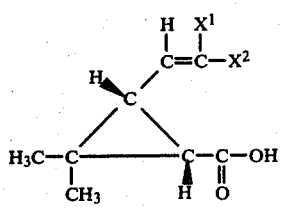
(II)

wherein $X^1$ and $X^2$ have the same meaning as in formula I-from mixtures of cis and trans carboxylic acids of formula II would be useful. A novel intermediate has now been found in such an isolation process.

SUMMARY OF THE INVENTION

Accordingly, the present invention provides cis-lactones of the general formula:

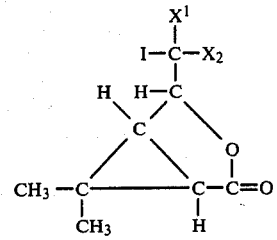

wherein each of the groups $X^1$ and $X^2$ represents a fluorine, chlorine or bromine atom or a hydrocarbyl group. Examples of hydrocarbyl groups that $X^1$ and $X^2$ may represent are alkyl, cycloalkyl and aromatic groups of up to 8 carbon atoms, such as methyl, ethyl, propyl, phenyl, benzyl, phenethyl or the like. $X^1$ and $X^2$ preferably represent an alkyl group and particularly an alkyl group with fewer than five carbon atoms; most preferably, $X^1$ and $X^2$ each represent a methyl group, in other words cis-2-(1-iodo-1-methylethyl)-6,6-dimethyl-4-oxo-3-oxabicyclo[3.1.0]hexane is most preferred. Among the lactones of formula III, in which $X^1$ and $X^2$ each represent a fluorine, chlorine or bromine atom, cis-2-dichloroiodomethyl-6,6-dimethyl-4-oxo-3-oxabicylco[3.1.0]hexane is preferred, $X^1$ and $X^2$ both representing a chorine atom. Other examples of lactones of formula III are: cis-2-difluoroiodomethyl-6,6-dimethyl-4-oxo-3-oxabicyclo-[3.1.0]hexane, cis-2-dibromoiodomethyl-6,6-dimethyl-4-oxo-3-oxabicyclo[3.1.0]hexane, and cis-2-bromochloroiodomethyl-6,6-dimethyl-4-oxo-3-oxabicyclo[3.1.0]hexane.

The cis lactones of the general formula III are iodalactones and can be prepared in a manner known per se, for example as described in "Russian Chemical Reviews", 40 (3), 1971, 272–283 and "Methoden der organischen Chemie" (Houben-Weyl) Book VI/2 (1963) 611. A preferred process for the preparation of a cis-lactone of the general formula:

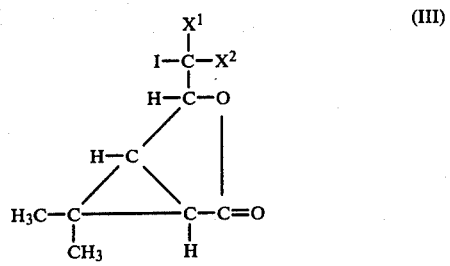
(III)

wherein each of the groups $X^1$ and $X^2$ represents a fluorine, chlorine or bromine atom or a hydrocarbyl group is characterized in that a cis acid of the general formula:

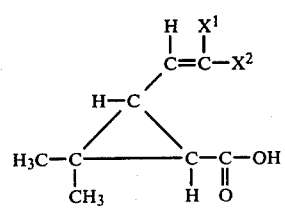
(IV)

wherein $X^1$ and $X^2$ have the same meaning as in the general formula III, or a salt thereof, is contacted with iodine in the presence of water and a base.

The salt of the compound of formula IV is an alkali metal, ammonium or tetra-alkyl-ammonium salt in which each alkyl is 1 to 10 carbon atoms, sodium, potassium, ammonium, tetra-methyl-ammonium, tetra-ethyl-ammonium salt or the like.

The base used in the reaction is suitably an alkali metal or ammonium carbonate, bicarbonate or hydroxide; ammonia or an amine. Amines include primary, secondary and, particularly tertiary amines, for example, tri-n-propylamine, tri-n-butylamine ethylmethyl-n-propylamine, tert-butyl-dimethylamine, dimethyloctadecylamine and pyridine. An alkali metal bicarbonate is preferred.

Preferred compounds of formula IV are those in which each of the groups $X^1$ and $X^2$ represents an alkyl group, particularly an alkyl group with fewer than five carbon atoms and most particularly, a methyl group. Among the compounds of formula IV, in which each of the groups $X^1$ and $X^2$ represents a fluorine, chlorine or bromine atom, chlorine atoms are preferred. Among the alkali metal hydrogen carbonates which can be used-i.e. lithium, sodium, potassium, rubidium and cesium hydrogen carbonate-sodium hydrogen carbonate is preferred.

The molar ratios of the iodine to the cis compound of the general formula IV and of the alkali metal hydrogen carbonate to this cis compound are not critical, but, preferably in the range of from 1 to 5, and particularly of from 1 to 1.5.

As the trans-acids corresponding to the cis-acids of the general formula VI do not enter into iodolactonizations the iodolactones of formula III can be used in the isolation of cis-carboxylic acids of formula VI from mixtures also containing the corresponding trans-isomers. The invention, therefore, also relates to the use of the iodo-lactones in the separation of cis-acids of formula II from mixtures with the corresponding trans-acids. For example, the cis-acid of formula VI can be separated from cis/trans mixtures by a process comprising converting the cis-acid content of the mixture into an iodo-lactone according to the invention, isolating the iodo-lactone so formed and reducing the lactone to the cis-acid by a method known per se. The iodolactonization of the cis-acid content of the mixture can be achieved by contacting the mixture with iodine in the presence of water and a base, preferably an alkali metal bicarbonate according to the procedure previously described with reference to the production of iodo-lactones.

The iodo-lactone usually appears as a precipitate from the aqueous solution of the salt (usually derived from the base employed) of the trans-acid. The iodo-lactone may be isolated from the reaction mixture by removing any excess iodine-for example by addition of alkali metal thiosulphate-followed by mechanical separation of the precipitated iodo-lactone, for example by filtration, centrifugation or decantation.

Thus, cis-2-(2,2-dichlorovinyl)-3,3-dimethylcyclopropanecarboxylic acid and cis-chrysantemumic acid-2,2-dimethyl-3-(2-methyl-1-propenyl)cyclopropanecarboxylic acid-can be isolated from mixtures with their trans isomers.

The cis-lactone of formula III may be reduced to the cis acid of the general formula IV with zinc and an acid, for example, acetic acid, propionic acid or hydrochloric acid. Very good results have been obtained with acetic acid. Alkanoic and mineral acids are also satisfactory.

It will be understood that the use of iodo-lactones can also be employed to separate (1R,cis)-acids from mixtures with the corresponding (1R,trans)-acids in the same way as they can be used to separate cis-acids from cis/trans-acids of formula VI. Also, it will be understood that the iodo-lactones of formula III can be derived from 1R,cis acids as well as being derived from cis acids of formula II.

The Examples further illustrate the invention. Yields and purities were determined by nuclear magnetic resonance (NMR) spectroscopy. The NMR data quoted were recorded at 90 MHz; the absorptions given are relative to a tetramethylsilane standard.

EXAMPLE I

Isolation of 1R, cis 2-(2,2-dichlorovinyl)-3,3-dimethylcyclopropanecarboxylic acid via 2-dichloroiodomethyl-6,6-dimethyl-4-oxo-3-oxabicyclo[3.1.0]hexane The contents of a 1-l flask equipped with a magnetic stirrer and thermometer and charged with 2-(2,2-dichlorovinyl)-3,3-dimethylcyclopropanecarboxylic acid (239 mmol, equal amounts of the cis and trans acids), sodium hydrogen carbonate (262 mmol), iodine (284 mmol, 36 g) and water (500 ml) were stirred at 70° C. for 24 hours. Then, sodium thiosulphate (32 mmol) was added and the precipitate present was filtered off and dissolved in dichloromethane (100 ml). The solution obtained was washed with three 20-ml portions of a saturated aqueous solution of sodium bicarbonate, the washed dichloromethane phase was dried over anhydrous magnesium sulphate and the solvent was evaporated from the dried liquid at sub-atmospheric pressure to leave a residue (39.3 g) of which the content of the title compound was 95% (yield 93%). The NMR spectrum of the title compound showed the following absorptions:

$\delta = 1.28$ ppm, singlet, C$\underline{H}_3$—C—CH$_3$
$\delta = 1.30$ ppm, singlet, CH$_3$—C—C$\underline{H}_3$
$\delta = 2.17$ ppm, doublet, $\underline{H}$C—C=O, J=6 Hz
$\delta = 2.30$ ppm, doublet, O=C—CH—C$\underline{H}$, J=6 Hz
$\delta = 4.30$ ppm, singlet, O—C$\underline{H}$ A 50-ml flask equipped with a magnetic stirrer and thermometer was charged with a solution of 2-dichloroiodomethyl-6,6-dimethyl-4-oxo-3-oxabicyclo[3.1.0]hexane (4 mmol) in a mixture of acetic acid (13 ml) and water (1 ml). Then, zinc powder (8 mmol) was added at a temperature of 10° C. and stirring was continued at 20° C. After one hour's stirring the zinc had dissolved, the clear solution obtained was poured out into water (50 ml), the mixture obtained was extracted with three 10 ml portions of dichloromethane, the combined extract phases were washed with water (25 ml portions), the washed organic liquid was dried over anhydrous magnesium sulphate and the solvent was evaporated from the dried liquid to leave a crystalline solid (0.87 g). The conversion of the starting lactone was 100%, with a selectivity to the title acid of more than 75%.

EXAMPLE II

Isolation of cis chrysantemumic acid via cis 2-(1-iodo-1-methylethyl)-6,6-dimethyl-4-oxo-3-oxabicyclo[3.1.0]hexane The contents of an NMR tube charged with 2,2-dimethyl-3-(2-methyl-1-propenyl)cyclopropanecarboxylic acid (chrysantemumic acid, 0.61 mmol, cis:trans ratio 36:64), sodium hydrogen carbonate (0.8 mol), iodine (0.48 mmol, 60 mg) and water (0.4 ml) were shaken for 15 minutes at 20° C. Then, the yellow precipitae formed was extracted with deuterochloroform (0.5 ml) from the reaction mixture obtained, the extract phase was washed with a saturated aqueous solution (0.3 ml) of sodium hydrogen carbonate and the washed solution was dried over anhydrous magnesium sulphate. The dried solution contained the title iodolactone with a purity of 85%. The NMR spectrum of the title lactone showed the following absorptions:

$\delta = 1.24$ ppm, singlet, $CH_3-CH-CH_3$ $\delta = 1.93$ ppm, singlet, $CH_3-CI-CH_3$ and 2.05 ppm, singlet, $CH_3-CI-CH_3$ $\delta = 2.0$ ppm, doublet, $HC-C=O$, $J = 6$ Hz $\delta = 2.17$ ppm, doublet, $HC-CH-C=O$, $J = 6$ Hz $\delta = 3.80$ ppm, singlet, $HC-O-$ The aqueous sodium hydrogen carbonate solution used for the above described washing was acidified with concentrated hydrochloric acid, the acidified solution was extracted with deuterochloroform (0.5 ml) and the extract phase obtained was dried over anhydrous magnesium sulphate. The dried extract phase contained pure trans 2,2-dimethyl-3-(2-methyl-1-propenyl)cyclopropanecarboxylic acid (trans chrysantemumic acid).

A 50-ml flask equipped with a magnetic stirrer and thermometer and surrounded by an ice bath was charged with a solution of the title iodolactone (3.5 mmol) in acetic acid (13 ml) and water (1 ml). Then, zinc powder (8 mmol) was gradually added over a period of 10 minutes. After the addition the ice bath was taken away and the temperature was allowed to adopt 20° C. One hour after the start the clear solution obtained was poured out into water (50 ml), the mixture obtained was extracted with three 10 ml portions of dichloromethane, the combined extract phases were washed with two 25-ml portions of water, the washed organic liquid was dried over anhydrous magnesium sulphate and the solvent was evaporated from the dried liquid at sub-atmospheric pressure to leave a solid residue (0.5 g) of which the content of cis chrysantemumic acid was 80%; trans-chrysantemumic acid could not be detected in the residue.

We claim:

1. A cis-lactone of formula III

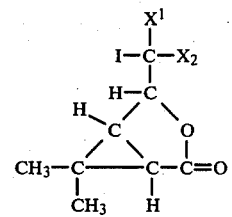

wherein $X^1$ and $X^2$ each represents an alkyl group containing fewer than five carbon atoms, phenyl, benzyl or phenethyl, substantially free of other stereoisomers.

2. A cis-Lactone according to claim 1 in which each of the groups $X^1$ and $X^2$ represents an alkyl group with fewer than five carbon atoms.

3. cis-2-(1-Iodo-1-methylethyl)-6,6-dimethyl-4-oxo-3-oxabicyclo[3.1.0]-hexane, substantially free of other stereoisomers.